(12) United States Patent
Lohmann et al.

(10) Patent No.: US 8,362,905 B2
(45) Date of Patent: Jan. 29, 2013

(54) RETRACTABLE ASSEMBLY

(75) Inventors: Martin Lohmann, Gerlingen (DE);
Rainer Schlereth, Neuss (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 645 days.

(21) Appl. No.: 12/448,348

(22) PCT Filed: Nov. 30, 2007

(86) PCT No.: PCT/EP2007/063077
§ 371 (c)(1),
(2), (4) Date: Dec. 18, 2009

(87) PCT Pub. No.: WO2008/077714
PCT Pub. Date: Jul. 3, 2008

(65) Prior Publication Data
US 2010/0109882 A1 May 6, 2010

(30) Foreign Application Priority Data

Dec. 21, 2006 (DE) .......................... 10 2006 061 815

(51) Int. Cl.
*G08B 17/00* (2006.01)
(52) U.S. Cl. ....................................... 340/584; 73/866.5
(58) Field of Classification Search .................. 340/584; 73/866, 866.5
See application file for complete search history.

(56) References Cited

U.S. PATENT DOCUMENTS 7,680,625 B2 * 3/2010 Trowbridge et al. ......... 73/866.5
2004/0069619 A1 * 4/2004 Koenemann et al. ......... 204/194
2005/0229727 A1 * 10/2005 Caderas ....................... 73/866.5

FOREIGN PATENT DOCUMENTS

| CN | 1637412 B | 8/2010 |
| DE | G 94 06 884.4 | 9/1994 |
| DE | 43 26 343 A1 | 2/1995 |
| DE | 10 2004 027 330 A1 | 2/2005 |
| DE | 20 2006 007 648 U1 | 8/2006 |
| EP | 0 372 121 A1 | 6/1990 |
| EP | 1 077 373 A2 | 2/2001 |
| EP | 1 248 102 A1 | 10/2002 |
| JP | 60-205345 | 10/1985 |
| JP | 4-118462 | 4/1992 |

(Continued)

OTHER PUBLICATIONS

International Search Report, Nov. 30, 2007.

(Continued)

*Primary Examiner* — John A Tweel, Jr.
(74) *Attorney, Agent, or Firm* — Bacon & Thomas, PLLC

(57) ABSTRACT

A retractable assembly, including an assembly housing and a tubular holder for a sensor guided in the assembly housing via a stroke movement linearly between a first position and a second position, wherein the sensor ascertains a physical and/or chemical process variable in a process, wherein an on-site electronics is provided, which ascertains as an actual value, or values, information concerning at least one other state variable of the retractable assembly, the process and/or the sensor, and wherein associated with the on-site electronics is a memory unit, in which the ascertained actual value, or values, is/are stored and/or predetermined desired values are stored.

12 Claims, 3 Drawing Sheets

FOREIGN PATENT DOCUMENTS

| | | |
|---|---|---|
| JP | 7-187686 | 7/1995 |
| JP | 11-6864 | 1/1999 |
| JP | 2002-218083 | 8/2002 |
| JP | 2004-132948 | 4/2004 |
| JP | 2004-219352 | 8/2004 |
| JP | 2004-233194 | 8/2004 |
| JP | 2005-234269 | 9/2005 |
| JP | 2006-85071 | 3/2006 |
| WO | WO 2004/023127 A1 | 3/2004 |
| WO | WO 2006/085071 A2 | 8/2006 |

OTHER PUBLICATIONS

German Search Report, Mar. 20, 2008.
English translation of IPR, Nov. 30, 2007.
German Search Report, Nov. 30, 2007.
International Search Report, Mar. 20, 2008.
Knick Elektronische Mesgeraete, The first digital pH sensor opens a new era in pH measurement, EMC News, 1994.
Endress Und Hauser: Cleanfit P CPA473, Feb. 2005.

\* cited by examiner

RETRACTABLE ASSEMBLY

TECHNICAL FIELD

The invention relates to a retractable assembly, including an assembly housing and a tubular, sensor holder guided in the assembly housing via a stroke movement linearly between a first position and a second position, wherein the sensor ascertains a physical and/or chemical process variable in a process. The sensors can be, for example, pH-electrodes, amperometric sensors, gas sensors, conductivity sensors, or the like.

BACKGROUND DISCUSSION

Retractable assemblies are widely used in analytical measurements technology. They serve for withdrawing sensors from, and then reintroducing them back into, a process, without process interruption, even in the presence of high process-pressures. The sensor is, in this connection, moved, automatically or manually, from a measuring position into a maintenance- or service-position, and then back into the measuring position. In the maintenance position, the sensor is checked, calibrated or, perhaps, simply cleaned, which, depending on the particular application, can be highly important for the quality of the measurements. In the measuring position, the process variable to be ascertained or monitored is sensed.

At process termination, or process interface, to the medium, two different solutions are in use. In a first form of embodiment, a ball valve, or a plug valve, is used, which, by turning, opens or closes to the process the opening, through which the sensor is moved into, and out of, the process. In a second form of embodiment, a closing plug is used. This closing plug is an integral component of the retractable assembly.

Ball valve assemblies are preferably used in the case of media containing a solids fraction. "Solids" include fibers, and, also, accreted lime and similar materials. The sensor in ball valve assemblies is moved into, and out of, the process separated from the closing-/opening mechanism. In this connection, the ball valve is, respectively, closed and opened. For the purpose of cleaning the sensor, the sensor is brought in the maintenance position into a rinsing chamber separated from the process.

Retractable assemblies are available from Endress+Hauser in different embodiments under the mark 'CleanFit'. Assemblies with a closing plug are, for example, carried under the identifiers Clean Fit S, CPA 471, CPA 472, CPA 473 and CPA 474. In the case of these retractable assemblies, the holder for the sensor is itself embodied as a sealing element. The front part of the holder is in the form of a plug, which already seals radially during movement back to the process connection. The construction of the sealing system of the assemblies CPA 471 and CPA 472 assures, in such case, a perfect separating of the rinsing chamber and, thus, the "outside world", and the process—and, indeed, in every position of the holder.

Of course, this separating is only effective, when the sealing rings are not damaged. A diligent checking of the sealing rings is, consequently, highly recommended. However, checking means, in the case of many assemblies, disassembling the complete retractable assembly and is, thus, burdened with considerable consumption of time. Also, it is to be heeded, that the checking, or replacing, of the sealing rings is to be performed only by schooled personnel, since the retractable assembly must then again work correctly under the reigning process conditions.

A replacement of the sealing rings is necessary at certain time intervals for the purpose of assuring the sealing function, since O-rings, which are usually made of polymers, after a certain amount of service time, tend to stick to a surface, against which they are pressed. If, then, the holder moves relative to the assembly housing, there is the danger, that the surface of the polymer, thus the O-ring, will be damaged. This effect is known under the name, "slip-stick effect". Upon occurrence of the effect, the sealing function of an O-ring is no longer assured.

From the above discussion, it becomes clear, that the number of stroke movements has a relatively large influence on the functioning of the sealing rings and, therewith, on the state of sealing of the retractable assembly. Other influencing variables as regards wear of the sealing rings are temperature and pressure. In the past, these variables have not been taken into consideration in the setting of maintenance intervals. Rather, separation of consecutive maintenance intervals has been based on empirical estimates.

SUMMARY OF THE INVENTION

An object of the invention is to provide an intelligent retractable assembly, which is able to perform self-diagnosis.

The object is achieved by the features that: an on-site electronics is provided, which ascertains, as actual value, or values, information concerning at least one other state variable of the retractable assembly, the process and/or the sensor; and, associated with the on-site electronics, is a memory unit, in which the ascertained actual value, or values, is/are stored. The actual value can be, for example, the number of stroke movements performed by the retractable assembly, the temperature of the retractable assembly or the process, the process pressure, the pressure in the pressure supply line of the retractable assembly, etc.

According to the invention, thus, a digitized retractable assembly is involved. Preferably, the retractable assembly is, furthermore, equipped with a unique identification. In this way, among other things, retractable-assembly-specific tracing of service incidents becomes possible in simple manner.

In an advantageous, further development of the retractable assembly of the invention, the on-site electronics is arranged in an electronics module, or in an electronics box. The electronics module, or the electronics box, is either integrated into the retractable assembly, or the retractable assembly is subsequently retrofittable with the electronics module, or with the electronics box, so that also retractable assemblies already installed in the field can be equipped with the supplemental functionality of the invention.

In an advantageous embodiment of the retractable assembly of the invention, there is provided on the on-site electronics at least one interface, or plug connection, via which the on-site electronics exchanges information with a remote electronics of the measurement transmitter and/or via which the on-site electronics is provided with energy and/or via which the on-site electronics exchanges information and/or energy with a sensor electronics associated with the sensor. Via the interface, e.g. the on-site electronics is provided with energy, while the retractable assembly is preferably operated pneumatically, as before. An applicable technology is already used by the Endress+Hauser in a product available successfully under the mark, MEMOSENS. This known MEMOSENS-technology is incorporated herein by reference.

In an advantageous further development of the apparatus of the invention, it is provided, that the retractable assembly has a sensor plug, such as is already provided currently on MEMOSENS-sensors. This plug connects—such as already mentioned—the measurement transmitter with the on-site electronics in the retractable assembly. From the on-site electronics, there extends, further, a contactless plug connection to the sensor electronics. Thus, the digital retractable assembly is also compatible with a non-digital retractable assembly. This embodiment is, insofar, advantageous, as only one connecting line must be provided from the measurement transmitter to the retractable assembly. The connection can naturally also be effected with electrical contacts.

A preferred form of embodiment of the retractable assembly of the invention provides at least one detector, which detects a stroke movement of the tubular holder in the retractable assembly; the control/evaluation unit makes available the number of completed stroke movements as actual value and/or it generates a warning report, when the number of the stroke movements reaches or exceeds a number of stroke movements predetermined as desired value. This warning report is taken to mean, that the retractable assembly must be subjected to maintenance, or that it is time for the sealing rings to be replaced. The retractable assembly of the invention is, thus, equipped with means, which permit predictive maintenance; that is to say, especially, that maintenance need only take place, when it is actually required. In this way, operating costs can be reduced; functionality of the retractable assembly is assured at all times.

The on-site electronics is connected with the control/evaluation unit, which is arranged in the measurement transmitter. Especially, it is provided, that the retractable assembly is equipped with a sensor plug, especially a contactless sensor plug. As soon as the number of performed stroke movements reaches a predetermined number of stroke movements, the control/evaluation unit generates a report, that a predetermined number of stroke movements has occurred. This report is either output on a display or forwarded to a superordinated control station. Of course, it is also possible to equip the on-site electronics, or the electronics module, with a display. An option is, naturally, also, to equip the electronics module, or the on-site electronics, with a radio module, so that data-exchange can occur wirelessly. In this way, the retractable assembly is relatively insensitive to rinse water and corrosive vapors.

Preferably, the detectors are two end position switches, which detect the reaching of the first position—the measuring position—and the second position—the maintenance position—of the tubular holder.

As already indicated, besides the mechanical stroke movements, also other state variables in the environment of the retractable assembly influence time between maintenance intervals. Therefore, according to an advantageous further development of the retractable assembly of the invention, at least one temperature sensor is provided, which ascertains the temperature of the retractable assembly and/or the process, and that the control/evaluation unit stores in the memory unit the maximum measured temperature value and/or the period of time, during which temperature is above a predetermined threshold value.

As already mentioned, the current number of stroke movements performed since last maintenance and/or an indication for replacement of a wear component of the retractable assembly are/is displayed, as soon as the number the stroke movements reaches a predetermined, desired value. Of course, the achievable number of stroke movements depends strongly on temperature and pressure, so that the desired-number of stroke movements is ascertained, preferably, as a function of these two variables.

As already mentioned above, actuation of the retractable assembly occurs manually or automatically via a pneumatic actuating unit, which moves the tubular holder for the sensor in the retractable assembly between the first position and the second position, or between the second position and the first position.

In the case of automatic actuation of the retractable assembly, according to an advantageous embodiment of the apparatus of the invention, a timer is provided, which ascertains the time period, which the tubular holder requires for travelling the distance between the first position and the second position. In the memory unit, the time, which the retractable assembly needs for moving the sensor from the first position into the second position in the case of correct functioning of the retractable assembly, is stored as desired value. The control/evaluation unit generates a warning report, when the predetermined time period is reached or exceeded.

In order to improve the accuracy of the above described monitoring of the retractable assembly for the purpose of self-diagnosis, a first pressure sensor is provided, which detects pressure in a supply line of the pneumatic actuating unit. Additionally or alternatively, a second pressure sensor is provided, which ascertains pressure in the process; the control/evaluation unit corrects the time, predetermined as a desired value, as a function of the pressure measured in the supply line and/or in the process. Thus, it is assured, that a warning report is generated only when a worsening of the ability of the retractable assembly to function occurs.

An advantageous embodiment of the retractable assembly of the invention provides, in a connecting line of the pneumatic actuating unit, a pressure-to-current converter, which provides the on-site electronics and/or the sensor electronics with energy. This solution is an alternative to the embodiment, in which the on-site electronics is provided with energy from the measurement transmitter. With this embodiment of the invention, quasi, an intelligent, self-sufficient, retractable assembly is created, which also can be used without problem in an Ex-region.

Moreover, it is provided, that identification data and/or service measures as regards the retractable assembly are stored in the memory unit of the on-site electronics. Furthermore, it is provided, that an RF/ID tag is associated with the retractable assembly for the purpose of unique identification.

BRIEF DESCRIPTION OF THE DRAWINGS

The invention will now be explained in greater detail on the basis of the appended drawing, the figures of which show as follows.

DETAILED DISCUSSION IN CONJUNCTION WITH THE DRAWINGS

Figure 1:
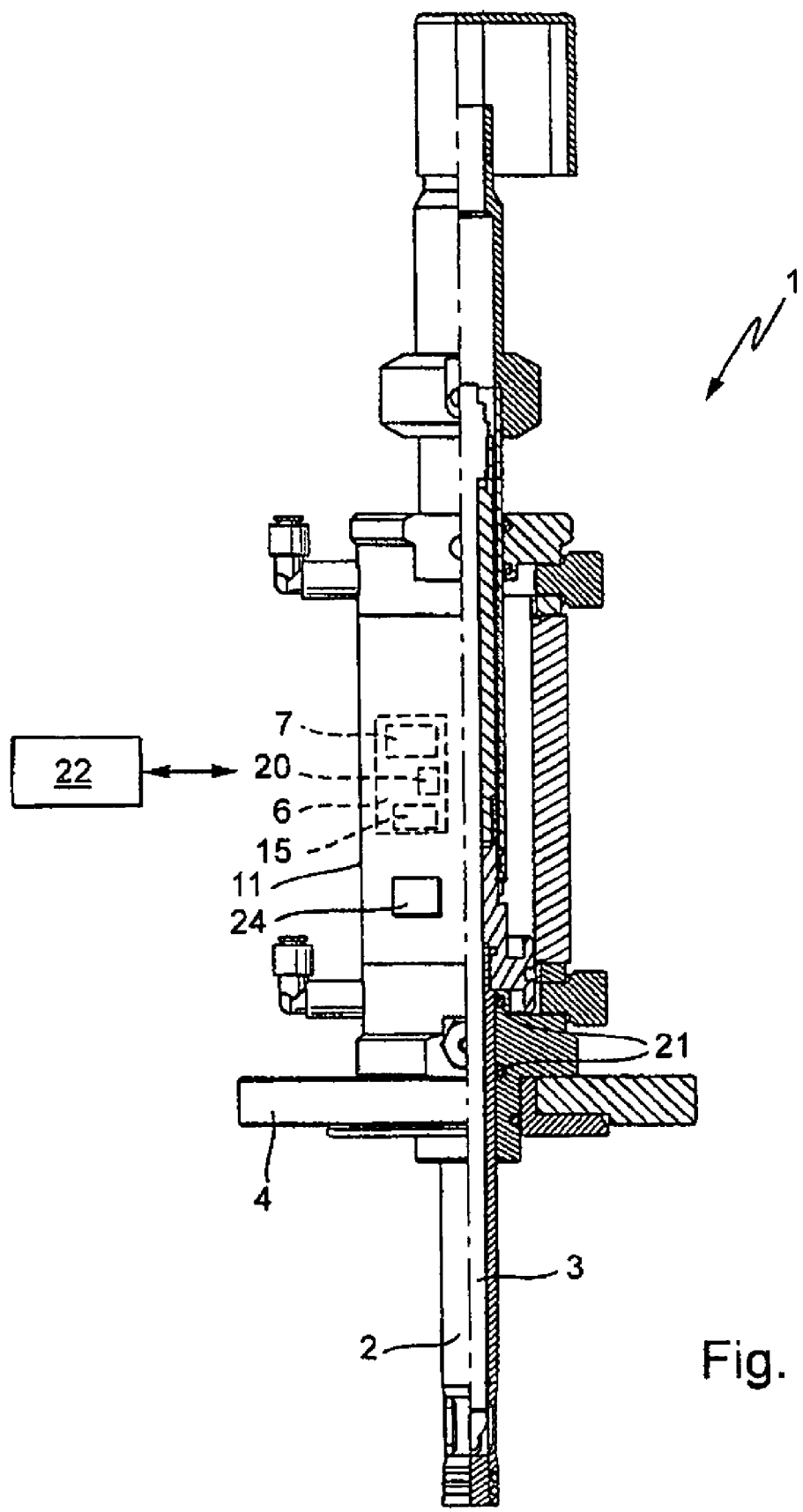
FIG. 1 partially in longitudinal section, an illustration of the retractable assembly of the invention.

FIG. 1 shows, partially in longitudinal section, an embodiment of the retractable assembly 1 of the invention. Retractable assembly 1 is secured via the flange 4 to a container (not separately shown in FIG. 1), in which the medium to be monitored is located. The sensor 3 is positioned in a tubular holder, the so-called sensor holder 2. The sensor holder 2 serves for protecting the relatively sensitive sensor 3 in contact with the medium. Sensor 2 is, for example, a pH-electrode. The retractable assembly 1 is shown in FIG. 1 in the measuring position, wherein the sensor 3 is in contact with the medium. Retractable assembly 1 is so embodied, that the sensor 3 is moved automatically back and forth between the measuring position and the maintenance position. In the maintenance- or service-position, sensor 3 is e.g. calibrated and/or cleaned. The retractable assembly 1 is driven via a known pneumatic actuating unit 22.

For moving the sensor 3, preferably, a pneumatic, actuating unit 22 is applied. Without the application of suitable protective measures, there is the danger, that deposits form on the sensor holder 2, which in the extreme case can lead thereto, that the sensor holder 2 can no longer move in the retractable assembly 1. Deposits on the movable parts degrade the ability of the retractable assembly 1 to function or, in the worst case, shut it down completely. Especially during use of the retractable assembly 1 and the sensor 3 in very dirty media, a regular cleaning of the sensor 3 is absolutely required.

Such deposits on the moved parts can be detected, for example, indirectly and early, via a creeping lengthening of the time required for moving the sensor holder 2 from one position into the other. In order, here, to have a high degree of safety, an embodiment of the retractable assembly 1 of the invention provides that the pressure in a supply line 18a, 18b to the pneumatic actuating unit 22 is taken into consideration. Preferably, by means of a timer 20, the time is monitored, which is needed, in order to move the sensor 3 from one position into the other position. The timer 20 is likewise, such as the memory unit 15, arranged in the on-site electronics 6. If the time period between the initializing of a stroke movement and the reaching of the end position exceeds a predetermined length of time, then a warning report is presented on the display 7. Alternatively or in addition, the warning report can be sent via a radio interface to a superordinated control station.

Figure 2:
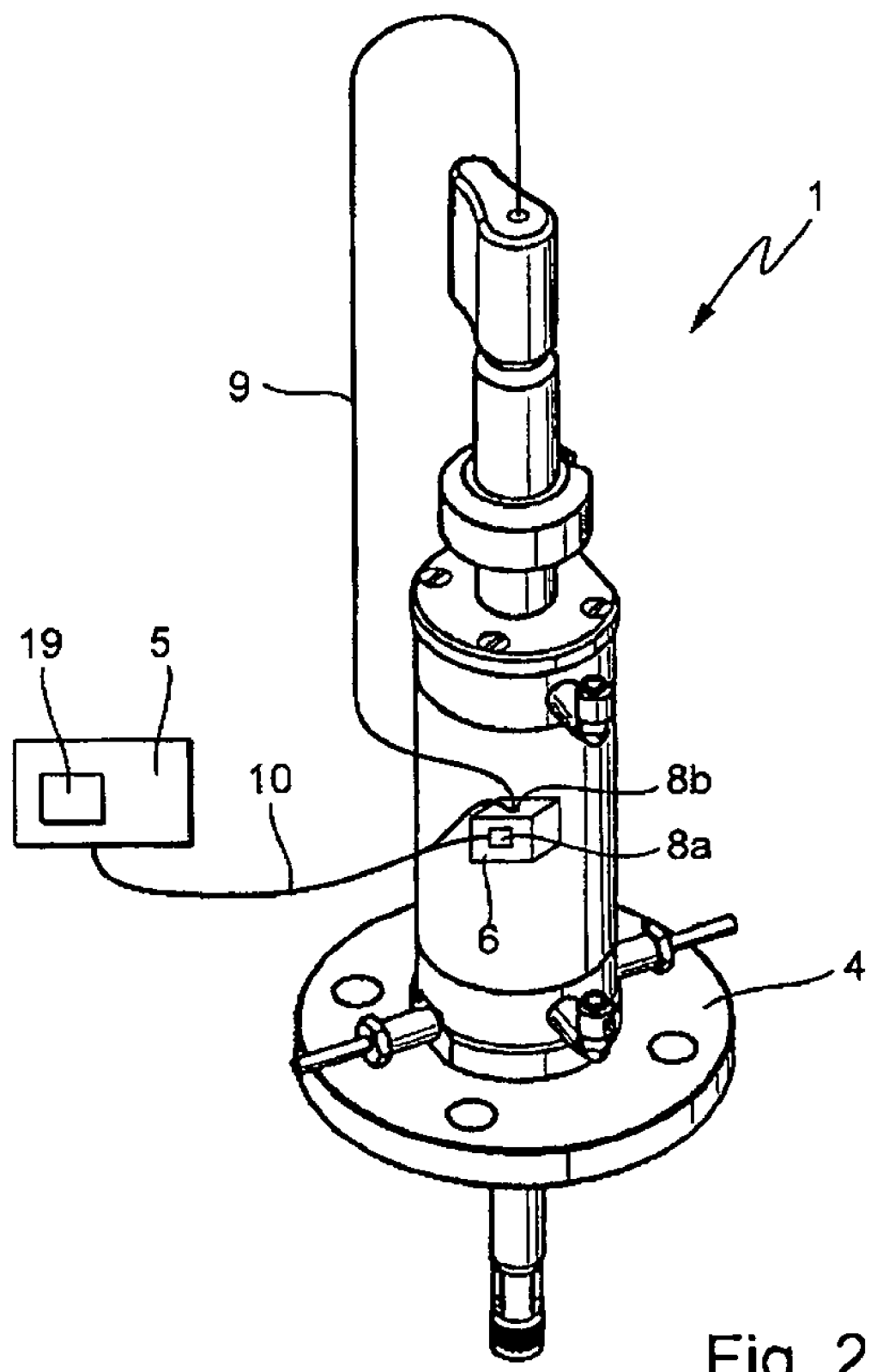
FIG. 2 a perspective view of the retractable assembly of the invention.

FIG. 2 shows a perspective view of the retractable assembly 1 of the invention. Again, the retractable assembly 1 of the invention is equipped with the on-site electronics 6. The retractable assembly 1 has a plug, or a plug connection, 8a, similar to the plugs, such as are already currently in use in connection with the MEMOSENS-technology. Via this plug 8a and the connecting line 10, the on-site electronics 6 is connected with the measurement transmitter 5. Arranged in the measurement transmitter 5 is the control/evaluation unit 19. Plug 8a is so embodied that data transfer and energy supply to the on-site electronics 6 occur, in the illustrated case, inductively according to the known MEMOSENS-technology. Extending from the on-site electronics 6, a contactless plug connection 8b leads, in the illustrated case, via the connecting line 9 to the sensor electronics 23. Of course, alternatively to the contactless plug connection 8a; 8b, also an electrical contacting via plug contacts can occur.

This above described embodiment is, thus, advantageous, since, here, only one connecting line 10 must be provided from the measurement transmitter 5 to the retractable assembly 1. The usually necessary connecting line between measurement transmitter 5 and sensor electronics 23 can be omitted. Of course, the one connecting line from the measurement transmitter 5 can also be moved to the sensor electronics 23.

Figure 3:
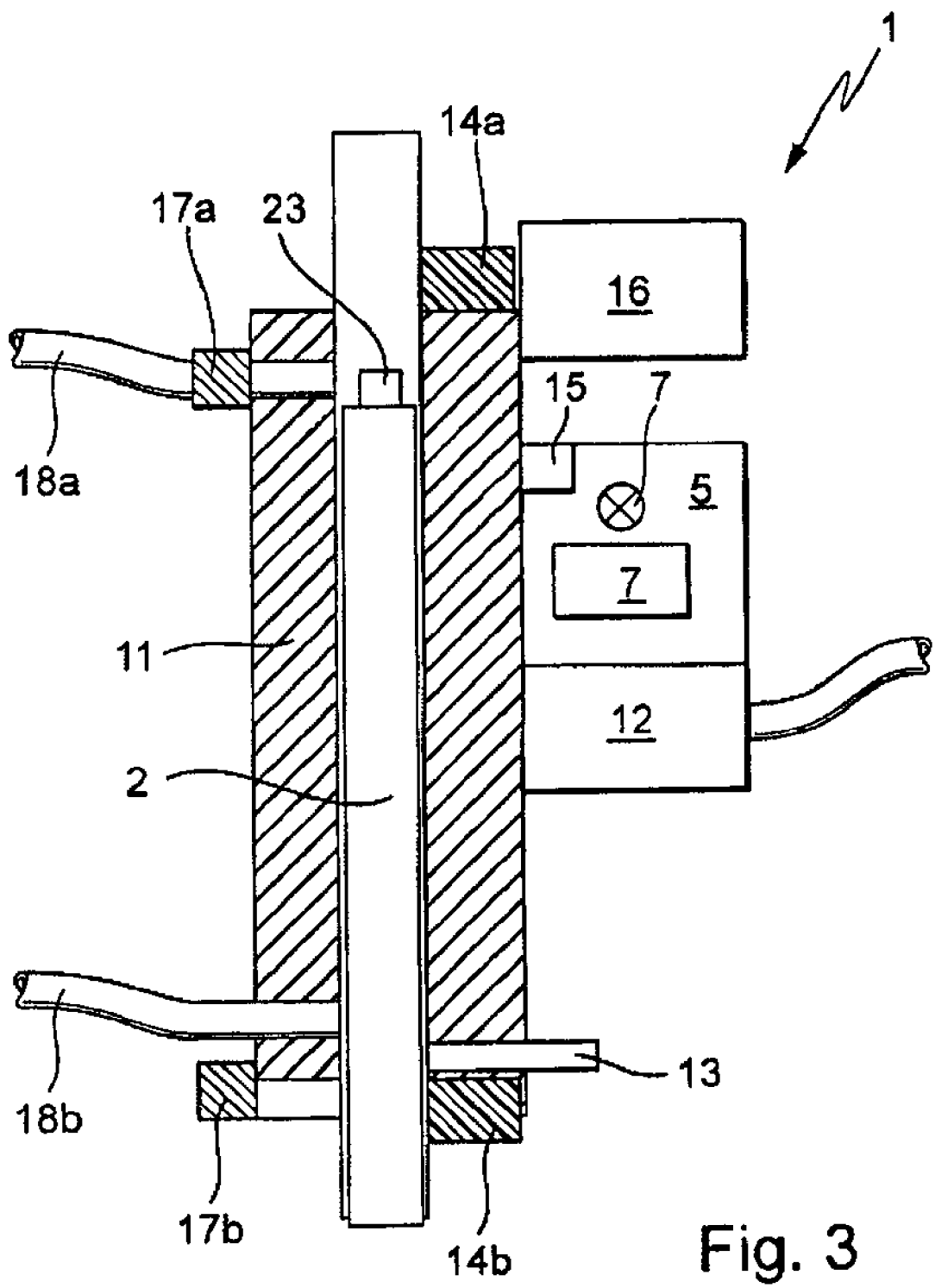
FIG. 3 a schematic drawing of a preferred embodiment of the retractable assembly of the invention.

FIG. 3 shows a schematic drawing of a preferred embodiment of the retractable assembly 1 of the invention. Retractable assembly 1 is so optimized, that, through monitoring of different state variables in the system, at the sensor 3 or in the process, it enables predictive maintenance. The state variables of the system (thus the retractable assembly 1) include, for example, the number of stroke movements, through which the sensor 3 is moved from the measuring—into the maintenance-position. The stroke movements are registered via the two end position switches 14a, 14b.

Information concerning the state variable, temperature, in the retractable assembly 1 is delivered by the temperature sensor 13. Information concerning the pressure in the supply line 18a of the pneumatic actuating unit is provided via the pressure sensor 17a. The process pressure is registered via the pressure sensor 17b.

The currently ascertained state variables are compared by the on-site electronics 6 with predetermined desired values. Alternatively or in addition, the ascertained state variables are stored in the memory unit 15 e.g. as historical data. If, for example, a predetermined number of stroke movements is reached, then a warning report is sent for showing on the display 7, or the warning report is forwarded via the connecting line 10 to the measurement transmitter 5 and output there in suitable manner. The warning report gives the operating personnel an indication, that the sealing rings on the retractable assembly 1 must be replaced. If, furthermore, the temperature influence on the wear components of the retractable assembly 1 is known, then a prognosis can be output, concerning the point in time when the next replacement of the sealing rings 21 must probably be done.

The embodiment shown in FIG. 3 is equipped with an internal energy production-unit 12 for operating the on-site electronics 6. The on-site electronics 6 is embodied as a separate electronics module 6 with a display 7. The electronics module 6 can be retrofitted into the retractable assembly 1. The energy producing unit is, moreover, a pressure/current converter 12, which preferably is installed in a supply line 18a, 18b of the pneumatic actuating unit 22.

The invention claimed is:

1. A retractable assembly, comprising:
   a sensor;
   an assembly housing;
   a tubular holder for said sensor guided in said assembly housing via a stroke movement linearly between a first position and a second position; and
   on-site electronics,
   a control/evaluation unit, wherein:
   said sensor ascertains a physical and/or chemical process variable in a process;
   said on-site electronics ascertains, as an actual value, or values, information concerning at least one other state variable of the retractable assembly, the process and/or said sensor;
   associated with said on-site electronics is a memory unit, in which the ascertained actual value, or values, is/are stored and/or predetermined, desired values are stored;
   on the retractable assembly at least one detector, which detects a stroke movement of said tubular holder in the retractable assembly; and
   said control/evaluation unit provides a number of accomplished stroke movements as actual values and/or generates a warning report, when the number of stroke movements reaches a number of stroke movements predetermined as a desired value.

2. The retractable assembly as claimed in claim 1, wherein:
   said on-site electronics is arranged in an electronics module, or in an electronics box, and the electronics module, or the electronics box, is integrated into the retractable assembly or the retractable assembly is retrofittable with said electronics module, or with the electronics box.

3. The retractable assembly as claimed in claim 2, wherein:
   there is provided on said on-site electronics at least one interface, or a plug connection, via which said on-site electronics exchanges information with a remote measurement transmitter of said sensor and/or via which said on-site electronics is provided with energy and/or via which said on-site electronics exchanges information and/or energy with sensor electronics associated with said sensor.

4. The retractable assembly as claimed in claim 1, wherein:
said detectors comprise two end position switches, which detect reaching of the first position and the second position of said tubular holder.

5. The apparatus as claimed in claim 1, further comprising:
a pneumatic actuating unit, via which said tubular holder is movable in the retractable assembly between the first position and the second position, or between the second position and the first position.

6. The retractable assembly as claimed in claim 5, wherein:
provided in a supply line of said pneumatic actuating unit is a pressure-to-current converter, which provides said on-site electronics and/or said sensor electronics with energy.

7. The retractable assembly as claimed in claim 1, wherein:
stored in said memory unit of said on-site electronics are identification data and/or service measures.

8. The retractable assembly as claimed in claim 1, wherein:
an RF/ID-tag is associated with the retractable assembly.

9. A retractable assembly, comprising:
a sensor;
an assembly housing;
a tubular holder for said sensor guided in said assembly housing via a stroke movement linearly between a first position and a second position;
on-site electronics;
a control/evaluation unit;
at least one temperature sensor which ascertains the temperature of the retractable assembly and/or the process, and said control/evaluation unit stores, in a memory unit, maximum measured temperature-value and/or length of time, during which lies above a predetermined threshold value, wherein:
said sensor ascertains a physical and/or chemical process variable in a process;
said on-site electronics ascertains, as an actual value, or values, information concerning at least one other state variable of the retractable assembly, the process and/or said sensor; and
associated with said on-site electronics is said memory unit, in which the ascertained actual value, or values, is/are stored and or predetermined, desired values are stored.

10. A retractable assembly, comprising:
a sensor;
an assembly housing;
a tubular holder for said sensor guided in said assembly housing via a stroke movement linearly between a first position and a second position;
on-site electronics;
a control/evaluation unit;
at least one detector on the retractable assembly, which detects a stroke movement of said tubular holder in the retractable assembly; and
a display device on which the actual value of the number of stroke movements and/or an indication for replacement of a wear component of the retractable assembly is displayed, when the number of stroke movements reaches a predetermined, desired value, wherein:
the desired value of stroke movements can be dependent on temperature;
said at least one detector comprises two end position switches, which detect reaching of the first position and the second position of said tubular holder;
said control/evaluation unit provides a number of accomplished stroke movements as actual and/or generates a warning report, when the number of stroke movements reaches a number of stroke movements predetermined as a desired value;
said sensor ascertains a physical and/or chemical process variable in a process;
said on-site electronics ascertains, as an actual value, or values, information concerning at least one other state variable of the retractable assembly, the process and/or said sensor; and
associated with said on-site electronics is a memory unit, in which the ascertained actual value, or values, is/are stored and/or predetermined, desired values are stored.

11. A retractable assembly, comprising:
a sensor;
an assembly housing;
a tubular holder for said sensor guided in said assembly housing via a stroke movement linearly between a first position and a second position;
on-site electronics;
a control/evaluation unit;
a timer, which ascertains the length of time required for said tubular holder to travel between the first position and the second position, wherein:
said sensor ascertains a physical and/or chemical process variable in a process;
said on-site electronics ascertains, as an actual value, or values, information concerning at least one other state variable of the retractable assembly, the process and/or said sensor;
associated with said on-site electronics is a memory unit, in which the ascertained actual value, or values, is/are stored and/or predetermined, desired values are stored;
stored in said memory unit as a desired value is the length of time needed by the retractable assembly for moving said sensor from the first position into the second position in the case of correct functioning of the retractable assembly; and
said control/evaluation unit generates a warning report, when the predetermined time period is reached or exceeded.

12. The retractable assembly as claimed in claim 11, further comprising:
a first pressure sensor, which detects the pressure in a supply line of said pneumatic actuating unit, and/or
a second pressure sensor, which ascertains the pressure in the process, and said control/evaluation unit corrects, as a function of pressure measured in the supply line and/or in the process, the length of time predetermined as a desired value.

* * * * *